US009161742B2

(12) United States Patent
Neasham et al.

(10) Patent No.: US 9,161,742 B2
(45) Date of Patent: Oct. 20, 2015

(54) ULTRASOUND IMAGING APPARATUS (71) Applicant: University of Newcastle upon Tyne, Tyne and Wear (GB)

(72) Inventors: Jeffrey Alan Neasham, Tyne and Wear (GB); David James Graham, Northumberland (GB)

(73) Assignee: UNIVERSITY OF NEWCASTLE UPON TYNE, Tyne and Wear (GB)

( * ) Notice: Subject to any disclaimer, the term of this patent is extended or adjusted under 35 U.S.C. 154(b) by 141 days.

(21) Appl. No.: 13/974,483

(22) Filed: Aug. 23, 2013

(65) Prior Publication Data

US 2014/0276067 A1 Sep. 18, 2014

(30) Foreign Application Priority Data

Mar. 13, 2013 (GB) .................................. 1304498.7

(51) Int. Cl.
*A61B 8/00* (2006.01)
*A61B 8/08* (2006.01)
*A61B 5/00* (2006.01)
*A61B 8/14* (2006.01)

(52) U.S. Cl.
CPC ............... *A61B 8/5207* (2013.01); *A61B 5/725* (2013.01); *A61B 8/14* (2013.01); *A61B 8/42* (2013.01); *A61B 8/4209* (2013.01); *A61B 8/4245* (2013.01); *A61B 8/4254* (2013.01); *A61B 8/4411* (2013.01); *A61B 8/4461* (2013.01); *A61B 8/4483* (2013.01)

(58) Field of Classification Search
USPC ........................................................ 600/446
See application file for complete search history.

(56) References Cited

U.S. PATENT DOCUMENTS

| 4,030,344 | A | * | 6/1977 | Northeved et al. ............... 73/620 |
| 5,152,294 | A | * | 10/1992 | Mochizuki et al. ........... 600/459 |
| 5,460,179 | A | * | 10/1995 | Okunuki et al. ............... 600/444 |
| 5,722,412 | A | * | 3/1998 | Pflugrath et al. ............... 600/459 |
| 6,120,452 | A | | 9/2000 | Barthe et al. |
| 7,823,454 | B2 | | 11/2010 | MacLauchlan et al. |
| 8,409,102 | B2 | | 4/2013 | Griffin et al. |
| 2002/0138004 | A1 | | 9/2002 | Dickey et al. |
| 2007/0276249 | A1 | * | 11/2007 | Abascal ......................... 600/459 |

(Continued)

FOREIGN PATENT DOCUMENTS

JP 11-318892 11/1999
WO WO2008/131722 11/2008

(Continued)

OTHER PUBLICATIONS

Li et al (Design and fabrication of a miniaturized integrated, high frequency acoustical lens transducer system, 2002).*

(Continued)

*Primary Examiner* — Joel F Brutus
(74) *Attorney, Agent, or Firm* — Marvin Petry; Stites & Harbison PLLC (57) ABSTRACT

An ultrasound imaging apparatus including a processing unit configured to produce an ultrasound image of the target region by applying position/orientation data representative of the position and/or orientation of an ultrasound transducer on the first side of a surface during each collection cycle to echo data representative of reflected ultrasound energy received by the ultrasound transducer during each collection cycle so as to coherently focus the echo data at a plurality of points distributed within the target region.

21 Claims, 5 Drawing Sheets

(56) References Cited

U.S. PATENT DOCUMENTS

2010/0324418 A1 12/2010 El-Aklouk et al.
2012/0046548 A1 2/2012 Hao et al.

FOREIGN PATENT DOCUMENTS

WO WO2014/114512 7/2014
WO WO2014/121858 8/2014

OTHER PUBLICATIONS

Châtillon, Jacques, et al., "SAMI: A Low-Frequency Prototype for Mapping and Imaging of the Seabed by Means of Synthetic Aperture", Jan. 1999, pp. 4-15, vol. 24, No. 1., IEEE Journal of Oceanic Engineering.

Trots, Ihor, et al., "Multi-Element Synthetic Transmit Aperture in Medial Ultrasound Imaging", Jan. 1, 2010, pp. 687-699, vol. 35, No. 4, Archives of Acoustics.

* cited by examiner

ULTRASOUND IMAGING APPARATUS

This invention relates to ultrasound imaging apparatuses and associated devices and methods.

Ultrasound imaging apparatuses, that is, apparatuses for producing ultrasound images are well known. Such devices are typically used in a medical context, where their use is commonly referred to as "diagnostic sonography" or simply "ultrasonography". A common produce of diagnostic sonography is obstetric sonography in which ultrasound energy is used to produce images of an embryo or foetus in a mother's womb.

Modern ultrasound imaging apparatuses typically produce ultrasound images using echo data produced using a probe having a plurality of ultrasound transducers arranged in a fixed array. A problem with modern ultrasound imaging apparatuses is that the multi-element transducer array and associated beamforming electronics typically used by such apparatuses are expensive to construct. This means that current "top-end" apparatuses are very expensive, e.g. in the range of £20,000-£100,000 (2012 prices).

The present invention has been devised in light of the above considerations.

The inventors have observed that it would be desirable to produce an ultrasound imaging apparatus using very low-cost components, whilst still being capable of producing ultrasound images of useful quality, e.g. so as to open up the possibility of using ultrasound imaging apparatuses in applications and/or regions where use of such apparatuses is currently cost prohibitive.

Accordingly, a first aspect of the invention may provide an ultrasound imaging apparatus including:

an ultrasound transducer configured to perform, in each of a plurality of positions and/or orientations on a first side a surface, a respective collection cycle in which the ultrasound transducer emits ultrasound energy into and receives reflected ultrasound energy from a target region on a second side of the surface that is opposite to the first side;

a processing unit configured to acquire echo data representative of reflected ultrasound energy received by the ultrasound transducer during each collection cycle and position/orientation data representative of the position and/or orientation of the ultrasound transducer on the first side of the surface during each collection cycle;

wherein the processing unit is configured to produce an ultrasound image of the target region by applying the position/orientation data to the echo data so as to coherently focus the echo data at a plurality of points distributed within the target region.

In this way, the inventors have found that an ultrasound image of acceptable quality, (see e.g. FIG. 5(a)(ii), FIG. 5(b)(ii) and FIG. 5(c)(ii)) can be produced using a single ultrasound transducer and without using the complex beam forming electronics normally required by modern ultrasound imaging apparatuses.

In the context of this disclosure, the term "ultrasound image" is intended to refer to any image produced using reflected ultrasound energy.

Similar focussing techniques are known in other technical fields, for example in radar (where such techniques are typically referred to as "synthetic aperture radar") and in sonar (where such techniques are typically referred to as "synthetic aperture sonar"), see e.g. "SAMI: a low-frequency prototype for mapping and imaging of the seabed by means of synthetic aperture", Chatillon, J., Adams, A. E., Lawlor, M. A., Zakharia, M. E., Oceanic Engineering, IEEE Journal of, pages: 4-15 Volume: 24, Issue: 1, January 1999.

However, as far as is known to the inventors, applying position/orientation data to coherently focus echo data acquired from a single ultrasound transducer in each of a plurality of positions and/or orientations on a first side a surface (e.g. by physically scanning the single ultrasound transducer across skin) is not a technique used in any existing medical ultrasound scanning products.

Preferably, the position/orientation data is applied to the echo data with the echo data being treated as if it had been acquired using a plurality of ultrasound transducers arranged in a fixed array so as to coherently focus the echo data at a plurality of points distributed within the target region. In this way, the processing unit can be seen as using the position/orientation data and the echo data to simulate echo data acquired by a fixed "synthetic" array of ultrasound transducers, even if the echo data was actually acquired using only a single ultrasound transducer element.

Preferably, the plurality of points are distributed at a plurality of depths within the target region. Preferably, the plurality of points are distributed throughout the entire target region.

The target region is preferably a 2 dimensional ("2D") region. The 2D region may lie in a plane that includes a predetermined path along which the ultrasound transducer is constrained to be moved relative to a housing (see below).

The ultrasound transducer is preferably included in an ultrasound probe.

Preferably, the ultrasound probe is separate from the processing unit, which may e.g. by a general purpose personal computer ("PC").

Preferably, the ultrasound probe is a hand-held ultrasound probe, i.e. suitable for being held in a hand of a user.

Preferably, the ultrasound probe includes a head to which the ultrasound transducer is mounted. The ultrasound transducer is preferably fixedly mounted to the head.

Preferably, the ultrasound probe also includes a housing to which the head is movably mounted so as to allow the ultrasound transducer to be moved relative to the housing.

More preferably, the head is movably mounted to the housing so as to allow the ultrasound transducer to be moved relative to the housing along a predetermined path. An advantage of this arrangement is that the predetermined path limits the number available positions and/or orientations of the ultrasound transducer on the first side of the surface during the collection cycles (assuming that the housing is kept substantially still with respect to the surface during the collection cycles) which generally makes it easier to produce an ultrasound image from the position/orientation data and the echo data.

Preferably, the ultrasound probe is manually operable, preferably with the head being movably mounted to the housing so as to allow the ultrasound transducer to be moved relative to the housing (preferably along a predetermined path, see above) by a hand of a user.

Alternatively the ultrasound probe may include a motorised mechanism configured to move the head relative to the housing (preferably along a predetermined path, see above).

Preferably, the head and housing are sized so that the housing can be held in a first hand of a user while the head is moved relative to the housing by a second hand of the user.

Preferably, the housing is configured to be kept substantially still with respect to the surface during each collection cycle. For example, the housing may be configured to be placed in contact with the surface (on the first side of the surface) so as to keep the housing substantially still with respect to the surface during each collection cycle.

The predetermined path could potentially have any shape, but is preferably curved or straight (e.g. for simplicity of calculation). The predetermined path preferably lies in a single plane (again, e.g. for simplicity of calculation).

Preferably, the predetermined path is curved. For example, the head may be rotatably mounted to the housing, e.g. by an axle, so as to allow the ultrasound transducer to be moved relative to the housing along a predetermined curved path. The curved path may be referred to herein as an arc.

The curved predetermined path may be convex or concave in relation to the surface. Preferably, the curved predetermined path is convex in relation to the surface, since this helps the ultrasound transducer to insonify (i.e. emit ultrasound energy into) a wider field of view e.g. compared with a straight predetermined path. In turn, this allows the ultrasound imaging apparatus to produce an ultrasound image of a larger target region e.g. compared with a straight predetermined path (albeit with a corresponding loss in image quality).

Preferably, the plurality of positions and/or orientations (in which collection cycles are performed by the ultrasound transducer) correspond to a plurality of predetermined locations on the predetermined path.

The ultrasound transducer may be configured to perform a collection cycle at each of the predetermined locations on the predetermined path based on a signal representative of a position and/or orientation of the head relative to the housing, e.g. as produced by a position and/or orientation determining unit described below.

Preferably, the predetermined locations on the predetermined path are uniformly spaced (e.g. for simplicity of calculation). However, in some embodiments, the predetermined locations on the predetermined path may be non-uniformly spaced.

In the case of the head being rotatably mounted to the housing, e.g. by an axle (see above), the ultrasound transducer may be configured to perform a collection cycle at each of the predetermined locations on the predetermined curved path based on a signal representative of an angle of rotation of the head relative to the housing, e.g. with the predetermined locations being separated by predetermined increments of rotation of the head relative to the housing, which predetermined increments may e.g. be 1° or less and are more preferably 0.5° or less.

Preferably, the distances between the predetermined locations on the predetermined path are small compared to a width of the ultrasound transducer, e.g. so that the "synthetic array" has a sufficient spatial sampling rate to avoid aliasing. For example, the average (e.g. mean) distance between the predetermined locations on the predetermined path may be half the width or less than the width of an ultrasound-emitting face of the ultrasound transducer. In this context, the width of the ultrasound-emitting face of the ultrasound transducer may be measured in a plane in which the predetermined path lies (see above).

Preferably, the processing unit is configured to produce a plurality of ultrasound images of the target region, wherein each ultrasound image is produced from position/orientation data and echo data acquired from a respective journey of the ultrasound transducer along the predetermined path.

Preferably, the processing unit is configured to produce each ultrasound image from position/orientation data and echo data acquired from a respective journey of the ultrasound transducer along the predetermined path regardless of the direction of movement of the ultrasound transducer along the predetermined path (e.g. which could be in a "forward" or "reverse" direction). This may help the apparatus to produce ultrasound images at a faster rate.

Preferably, the ultrasound transducer has a short focal length compared to the length of the imaged field, where focal length is defined as the distance from an ultrasound-emitting face of the ultrasound transducer to a point at which the amplitude of ultrasound energy observed is highest when the ultrasound transducer in use (this point is often referred to as "natural focus" of the ultrasound transducer).

For example, the ultrasound transducer may have a focal length of less than one tenth of the depth of the imaged field. For example, the ultrasound transducer may have a focal length of 5 mm or less in the plane of the image generation.

Preferably the ultrasound transducer has a large beam width, e.g. a beam width of 10 degrees or more (e.g. as measured in the plane of the predetermined path), where beam width may be defined as the angle between the half power points in the emitted acoustic field.

The ultrasound transducer may or may not include a focussing means, e.g. an acoustic lens, for bringing ultrasound energy produced by the ultrasound transducer to a focus. An ultrasound transducer with a focussing means may be referred to herein as a "focussed" ultrasound transducer. An ultrasound transducer without a focussing means may be referred to herein as an "unfocussed" ultrasound transducer. It is preferred that the ultrasound transducer included in an ultrasound imaging apparatus according to the first aspect of the invention is an unfocussed transducer, as this can help to reduce complexity and cost.

With a view to achieving a small focal length and large beam width, it is preferable for an unfocussed ultrasound transducer to have a small ultrasound-emitting face.

For example, the ultrasound-emitting face has a width of 3 mm or less, preferably as measured in a plane in which the predetermined path lies (see above), to achieve a large beam width in this plane.

Preferably, the ultrasound-emitting face has a length as measured in a plane perpendicular to the predetermined path that is longer than the width of the ultrasound-emitting face, e.g. to achieve a narrower beam in this plane. The length of the ultrasound-emitting face may be 12 mm or less and is preferably between 6 mm and 12 mm.

Preferably, the apparatus includes only a single ultrasound transducer. Preferably, the single ultrasound transducer includes only a single ultrasound transducer element.

The ultrasound imaging apparatus may include a position/orientation data unit configured to produce the position/orientation data representative of the position and/or orientation of the ultrasound transducer on the first side of the surface during each collection cycle, e.g. so that the position/orientation data can subsequently be acquired by the processing unit. The position/orientation data unit may be included in the ultrasound probe, and is preferably included in the head of the ultrasound probe (see above).

The position/orientation data unit may, for example, include a processing means, such as a microprocessor.

The position/orientation data unit may, for example, include a position and/or orientation determining unit for producing a signal representative of a position and/or orientation of the head relative to the housing. In this case, the processing means of the position/orientation data unit may be configured to produce the position/orientation data based on this signal.

If the head is rotatably mounted to the housing (see above), the position and/or orientation determining unit may be a rotary encoder configured to produce a signal representative of an angle of rotation of the head relative to the housing.

The ultrasound imaging apparatus may include an echo data acquisition unit configured to acquire the echo data representative of reflected ultrasound energy received by the ultrasound transducer during each collection cycle, e.g. so that the echo data can subsequently be acquired by the processing unit. The echo data acquisition unit may be included in the ultrasound probe, and is preferably included in the head of the ultrasound probe (see above).

The echo data acquisition unit may, for example, include a processing means, such as a microprocessor or programmable logic device. The processing means of the echo data acquisition unit may be configured to produce the echo data based on a signal (which may be a digital signal, see below) representative of reflected ultrasound energy received by the ultrasound transducer during each collection cycle.

The echo data acquisition unit may include an analogue to digital converter configured to convert an analogue signal representative of reflected ultrasound energy received by the ultrasound transducer during each collection cycle into a digital signal representative of reflected ultrasound energy received by the ultrasound transducer during each collection cycle. In this case, the processing means of the echo data acquisition unit may be configured to produce the echo data based on the digital signal. The analogue signal may be produced by or otherwise derived from an output of the ultrasound transducer.

Preferably, the echo data acquisition unit includes a bandpass filter for filtering the analogue signal before it reaches the analogue to digital converter.

In general, a bandpass filter is configured to attenuate frequencies below a lower band limit and above an upper band limit (which band limits may be defined by a frequency response of the transducer), whilst passing frequencies between these values. The difference between these band limits is usually referred to as the "bandwidth" of the bandpass filter.

Preferably, the analogue to digital converter is configured to convert the bandpass filtered analogue signal into the digital signal at a sample rate that is less than two times the bandwidth of the bandpass filtered analogue signal, e.g. using a bandpass sampling technique. Using a bandpass sampling technique in this context can significantly reduce the cost of the analogue to digital converter, whilst still allowing an accurate ultrasound image to be produced.

The echo data acquisition unit may also include one or more amplifiers configured to amplify the analogue signal before it reaches the analogue to digital converter.

A second aspect of the invention may provide a method corresponding to use of an apparatus according to the first aspect of the invention.

Accordingly, the aspect of the invention may provide a method of producing an ultrasound image, the method including:

performing, in each of a plurality of positions and/or orientations on a first side a surface, a respective collection cycle in which an ultrasound transducer emits ultrasound energy into and receives reflected ultrasound energy from a target region on a second side of the surface that is opposite to the first side;

acquiring echo data representative of reflected ultrasound energy received by the ultrasound transducer during each collection cycle and position/orientation data representative of the position and/or orientation of the ultrasound transducer on the first side of the surface during each collection cycle;

producing an ultrasound image of the target region by applying the position/orientation data to the echo data so as to coherently focus the echo data at a plurality of points distributed within the target region.

The method according to the second aspect of the invention may include any method step implementing or corresponding to any apparatus feature described in connection with any above aspect of the invention.

For example, the method may be performed using an ultrasound imaging apparatus according to the first aspect of the invention.

The method may include applying a fluid to a target area of the surface (e.g. skin) before performing the collection cycles.

A third aspect of the invention may provide an ultrasound probe as set out in the first aspect of the invention. Note that the ultrasound probe as set out in the first aspect of the invention need not include the processing means.

The ultrasound probe according to the third aspect of the invention may include any apparatus feature described in connection with any above aspect of the invention.

The invention also includes any combination of the aspects and preferred features described except where such a combination is clearly impermissible or expressly avoided.

Examples of our proposals are discussed below, with reference to the accompanying drawings in which.

Figure 1:
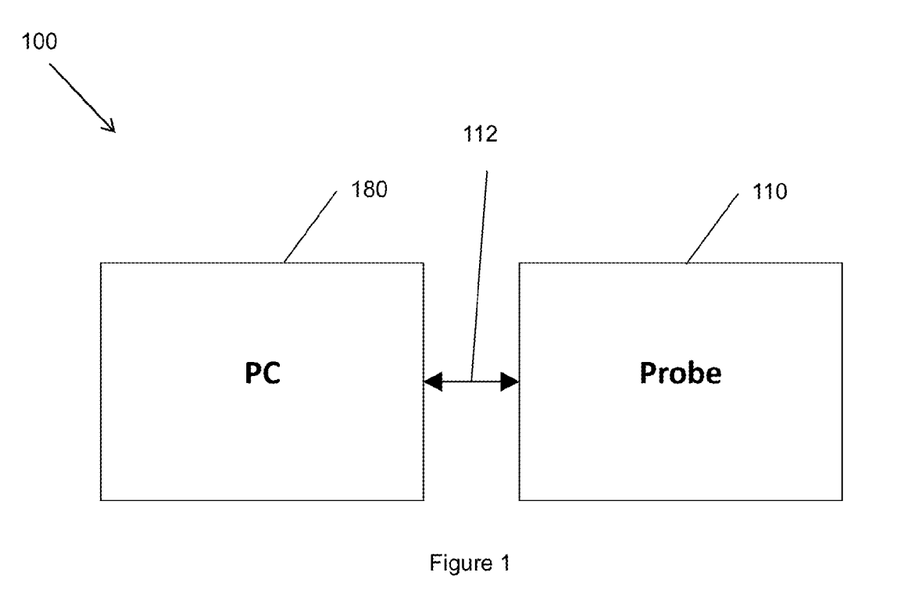
FIG. 1 is a schematic diagram showing an ultrasound imaging apparatus including an ultrasound probe and a processing unit.

As shown in FIG. 1, an ultrasound probe 110 is connected to a processing unit 180 by a cable 112. The processing unit 180 may e.g. be a general purpose personal computer ("PC") or mobile computing device.

Figure 2:
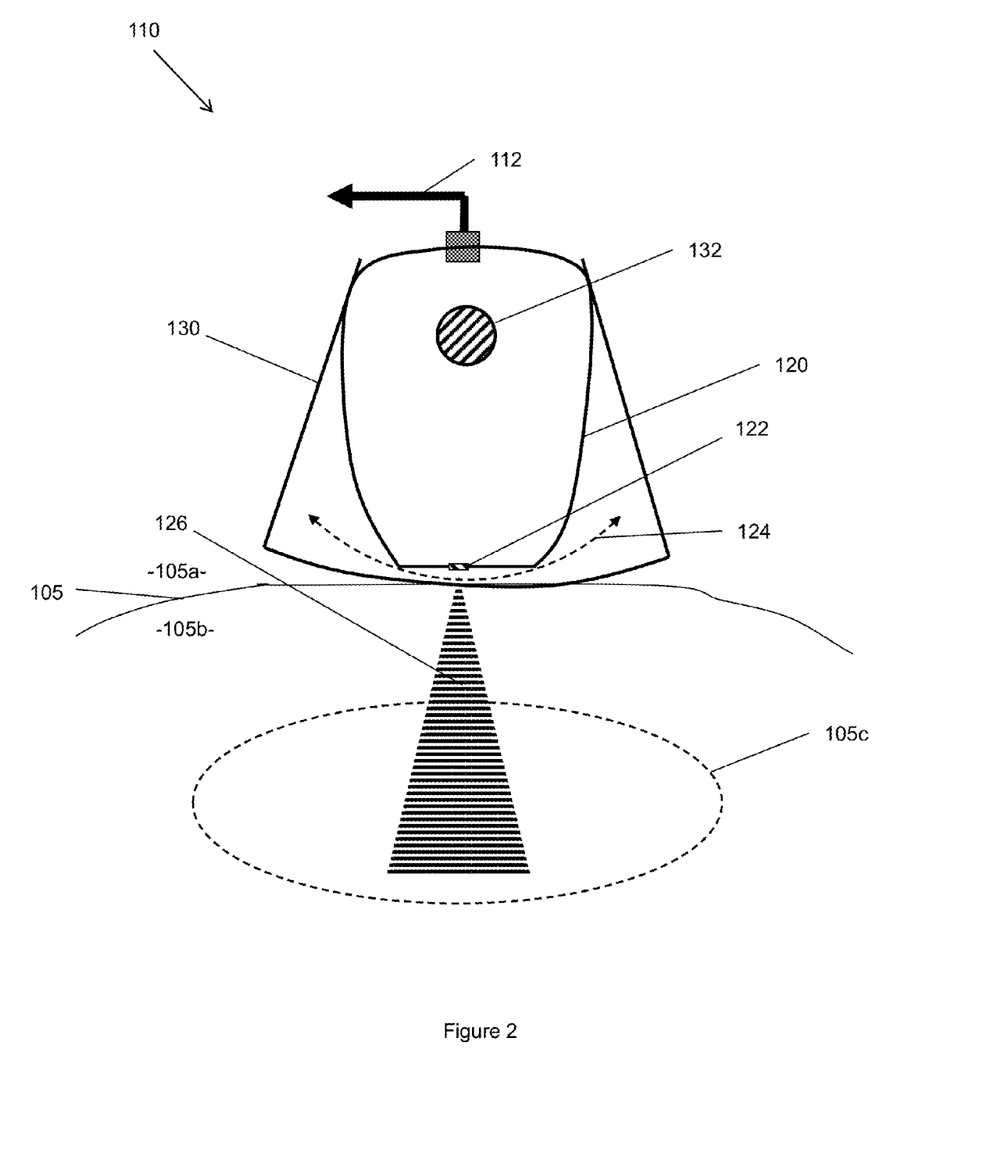
FIG. 2 shows the ultrasound probe of FIG. 1 in more detail.

FIG. 2 shows the ultrasound probe 110 of FIG. 1 in more detail.

Preferably, the ultrasound probe 110 includes a cable 112 for connecting the ultrasound probe 110 to the (otherwise separate) processing unit 180. The cable may be compliant with an industry standard for computer peripherals, e.g. a USB standard such as USB 2 or later.

Preferably, the ultrasound probe 110 is a hand-held probe and includes a head 120 on which a single ultrasound transducer 122 is fixedly mounted.

Preferably, the ultrasound probe 110 is manually operable and includes a housing 130 to which the head 120 is rotatably mounted by an axle 132 so as to allow the ultrasound transducer 122 to be moved relative to the housing 130 along a predetermined arc 124 by a hand of a user or by a motorised mechanism.

The radius of curvature is preferably between 50 mm and 100 mm to make the scan area appropriate for typical medical imaging applications and to make the device dimensions appropriate for hand gripping.

For the avoidance of any doubt it is to be noted that the hand of a user may move the ultrasound transducer 122 along the predetermined arc 124 by rotating the head 120 relative to the housing 130. That is, the hand of the user does not need to apply a force directly to the ultrasound transducer 122.

In FIG. 2, the ultrasound probe is shown as being located on a first side 105a of a surface 105, with the predetermined arc 124 being convex in relation to the surface 105 (when the housing 130 is placed in contact with the surface 105 with the ultrasound transducer 122 adjacent the surface 105). The surface 105 may, for example, be skin of patient, e.g. at an abdomen of a pregnant female patient. On a second, opposite, side 105b of the surface, there may be tissue of the patient.

Preferably, the ultrasound transducer 122 is configured to perform, in each of a plurality of positions and/or orientations on the first side 105a of the surface 105, a respective collection cycle in which the ultrasound transducer emits ultrasound energy into and receives reflected ultrasound energy from a target region 105c on the second side 105b of the surface 105. In FIG. 2, the ultrasound energy emitted by the ultrasound transducer 122 is shown as a beam 126 of ultrasonic energy (which may equally be referred to as an "ultrasonic beam").

Preferably, the housing 130 is configured to be kept substantially still with respect to the surface 105 during each collection cycle. For example, the housing 130 may be configured to be placed in contact with the surface 105 so as to keep the housing 130 substantially still with respect to the surface 105 during each collection cycle.

Preferably, the plurality of positions and/or orientations (in which collection cycles are performed by the ultrasound transducer 122) correspond to a plurality of predetermined locations on the predetermined arc 124.

Preferably, the ultrasound transducer 110 is configured to perform a collection cycle at each of the predetermined locations on the predetermined arc 124 based on a signal representative of an angle of rotation of the head 120 relative to the housing 130, e.g. with the predetermined locations being separated by predetermined increments of rotation of the head 120 relative to the housing 130. The predetermined increments of rotation are preferably small enough to ensure that the average distance between the predetermined locations on the predetermined arc 124 is less than a width of the ultrasound-emitting face of the ultrasound transducer 122 and may e.g. be 0.25°. The signal representative of an angle of rotation of the head 120 relative to the housing 130 may be produced by the rotary encoder 170 described below with reference to FIG. 4.

Each collection cycle is preferably performed very quickly such that the emitting and receiving of ultrasound energy can be assumed to occur at the same location on the predetermined arc 124, even if the head 120 is being moved whilst the collection cycle is performed. This may allow up to 3 journeys ("scans") of the ultrasound over the predetermined arc 124 per second, and hence 3 images to be produced per second by manual operation. Higher rates could be achieved with a motorised mechanism.

Figure 3:
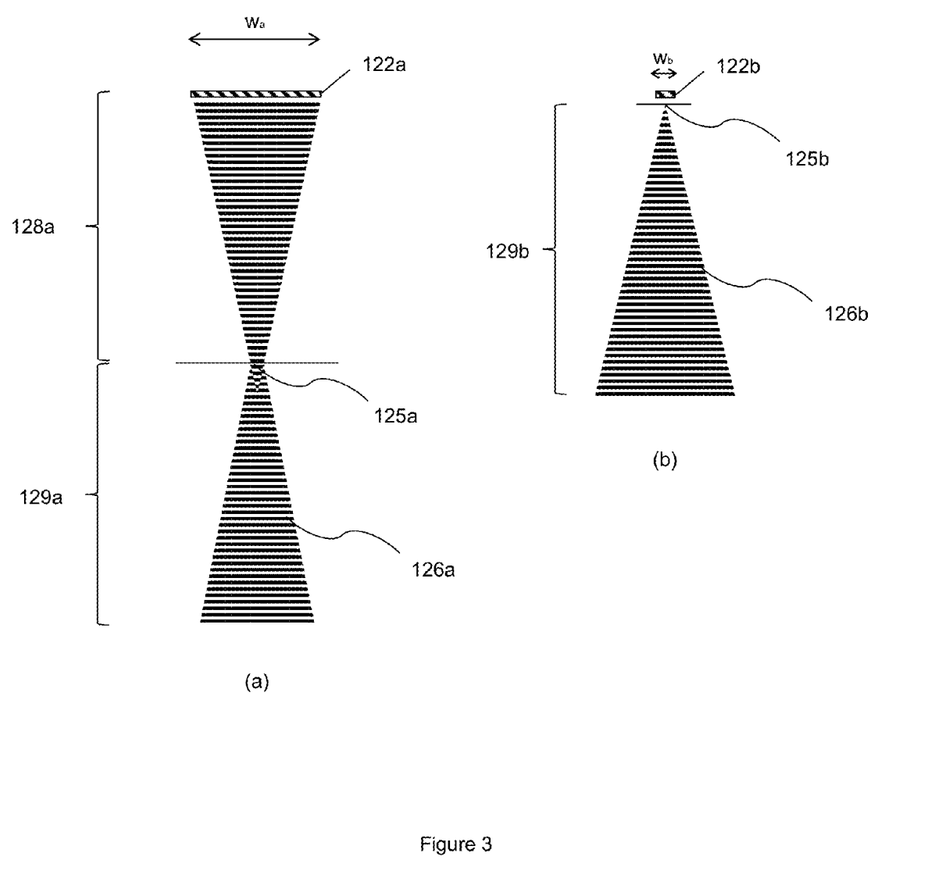
FIG. 3 is a diagram showing the effect of ultrasound transducer width on focal length for an unfocussed ultrasound transducer.

FIG. 3 is a diagram showing the effect of ultrasound transducer width on focal length for an unfocussed ultrasound transducer.

In FIG. 3(a), a first unfocussed ultrasound transducer 122a is shown that has an ultrasound-emitting face of a first width $w_a$.

As shown by FIG. 3(a), in use, the ultrasound-emitting face of the first ultrasound transducer 122a emits ultrasound energy in the form of a beam 126a of ultrasound energy. The beam 126a of ultrasound energy has maximum intensity at a "natural focus" 125a, at a distance from the ultrasound-emitting face that is usually referred to as the "focal length" of the first ultrasound transducer 122a. The focal length is proportional to the square of the transducer aperture size. The region between the ultrasound-emitting face of the first ultrasound transducer 122a and the point 125a of maximum intensity is usually referred to as the "near field" region 128a, with the region beyond the point 125a of maximum intensity usually being referred to as the "far field" region 129a.

For an unfocussed ultrasound transducer, such as the first ultrasound transducer 122a shown in FIG. 3(a), the amplitude of the ultrasound energy emitted by the ultrasound transducer in the near-field region 128a generally goes through a series of maxima and minima before reaching the point 125a of maximum intensity. In the far field region 129a, the amplitude of the ultrasound energy emitted by the ultrasound transducer generally decreases with increasing distance according to an inverse squared law.

In FIG. 3(b), a second ultrasound transducer 122b is shown that has an ultrasound-emitting face of a second width $w_a$, which is an order of magnitude smaller than the first width $w_a$.

A consequence of reducing the width of the ultrasound-emitting face of the second ultrasound transducer 122b is that the point of maximum intensity 125b is brought much closer to the ultrasound-emitting face of the second ultrasound transducer 122b. That is, as the width of the ultrasound-emitting face of the second ultrasound transducer 122b is reduced, the focal length of the second ultrasound transducer 122b is also reduced.

Preferably, the ultrasound transducer 122 used in the ultrasound probe 110 of FIG. 2 has an ultrasound-emitting face of width less than 10 signal wavelengths (as measured in the plane of the predetermined arc 124), so as to achieve an extremely short focal length, e.g. 5 mm or less. This means that field imaged by the ultrasound transducer 122 will, in effect, be entirely in the far field region, see e.g. FIG. 2.

In previous mechanically scanned ultrasound imaging apparatuses with single fixed focus transducers, operating with such a short focal length would result in poor angular resolution due to the large beam width in the far field region. Conversely whilst a larger transducer aperture would achieve smaller beam width in the far field, the longer focal length would place much of the target area in the near field region leading to severe distortions.

However, as described below in more detail, the processing unit 180 shown in FIG. 1 is preferably configured to produce an ultrasound image of the target region by focusing the position/orientation data and the echo data as if they are generated by the elements of a much larger array along the predetermined arc 124. In this way, consistently high angular resolution is achieved over the entire target area without significant near-field distortions.

Figure 4:
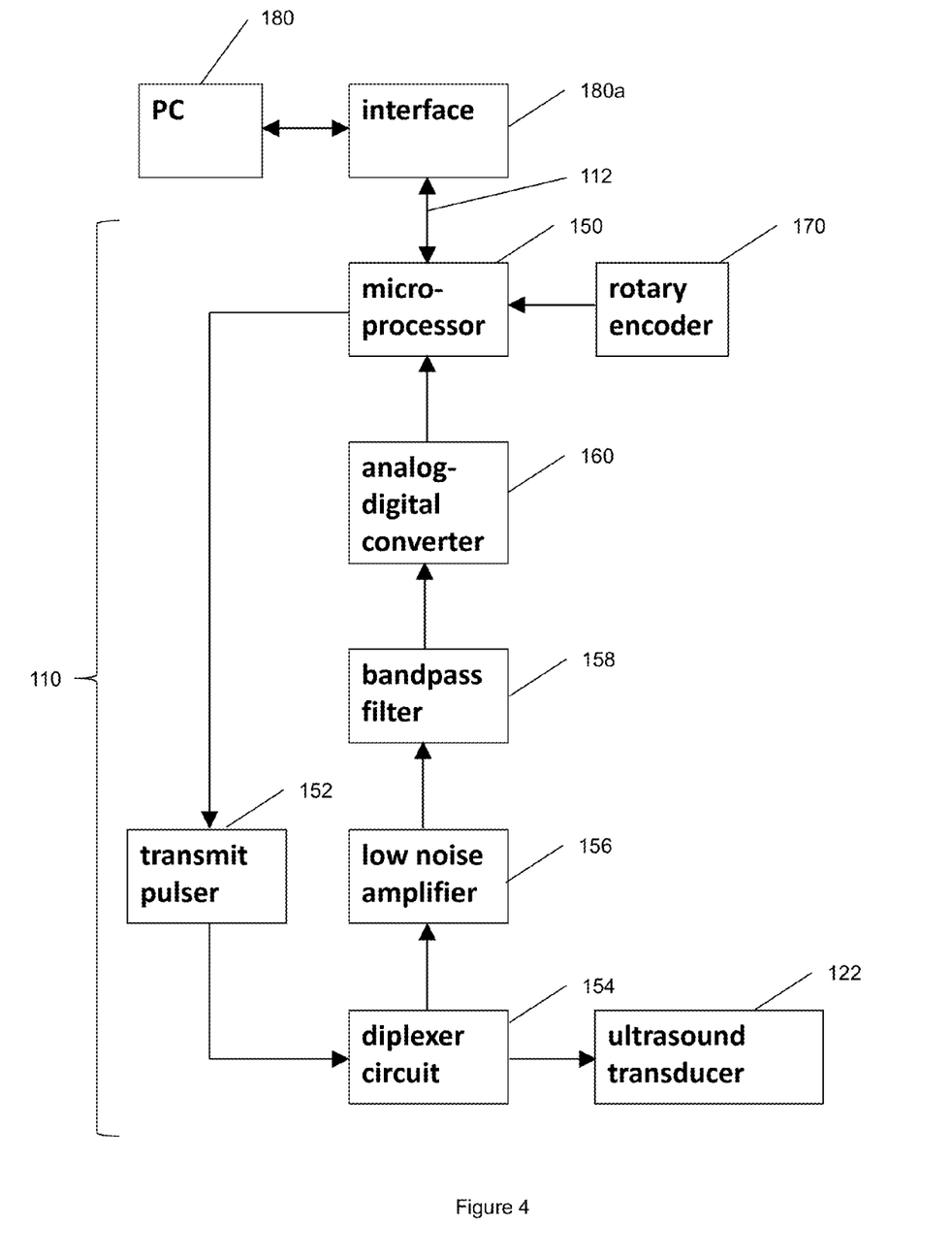
FIG. 4 is a schematic diagram showing electronic components of the ultrasound imaging apparatus of FIG. 1.

FIG. 4 is a schematic diagram showing electronic components of the ultrasound imaging apparatus 100 of FIG. 1.

In FIG. 4, the processing unit 180 is shown as including an interface 180a, e.g. a USB interface, for interfacing with the cable 112 of the ultrasound probe 110.

Electronic circuitry of the ultrasound probe 110 can be considered as being divided into four functional blocks: the ultrasound transducer 122; a transmitting unit; an echo data acquisition unit; and a position/orientation data unit. The electronic circuitry of the ultrasound probe 110 is preferably housed in the head 120 shown in FIG. 2.

The ultrasound transducer 122 preferably includes a single piezoelectric transducer element, preferably of PZT (lead zirconate titanate). As described above, the single piezoelectric transducer element preferably has a small width so that the ultrasound energy emitted by the ultrasound transducer 122 will generally be in the far field region at depths corresponding to the target region 105c. A focussing operation to obtain high resolution ultrasound images is preferably performed by software in the processing unit 180 (see below).

The transmitting unit preferably includes a microprocessor 150, a transmit pulser 152 and a diplexer circuit 154.

The echo data acquisition unit preferably includes the microprocessor 150, the diplexer 154, a low noise amplifier 156, a bandpass filter 158 and an analogue to digital converter 160.

The position/orientation data unit preferably includes the microprocessor 150 and a rotary encoder 170.

In use, a fluid is preferably applied to a target area of the surface 105, to create an acoustic impedance matching layer between the ultrasound transducer 122 and a target area of the surface, preferably with the housing being placed in contact with the surface so as to keep the housing substantially still with respect to the surface.

Next, the head 120 is rotated relative to the housing 130 so that the ultrasound transducer is moved along the predetermined arc 124, preferably with the microprocessor 150 initiating a collection cycle at each of the plurality of predetermined locations on the predetermined arc 124 based on a signal representative of an angle of rotation of the head 120 relative to the housing 130 produced by the rotary encoder 170.

On initiation of each collection cycle, the microprocessor 150 preferably controls the transmit pulser 152 to send an electric pulse to the ultrasound transducer 122 via the diplexer circuit. This electric pulse causes the ultrasound transducer to emit ultrasound energy from its ultrasound-emitting face in a pulse, e.g. of duration 1 microsecond or less.

Subsequently, an analogue (voltage) signal representative of reflected ultrasound energy received by the ultrasound transducer is preferably produced at the ultrasound transducer 122 by the piezoelectric effect. This analogue signal preferably passes through the diplexer circuit 154 at which point it is preferably amplified by the low noise amplifier 156.

Next, the bandpass filter 158 preferably attenuates frequencies in the analogue signal below a lower band limit (e.g. 3.6 MHz) and above an band limit value (e.g. 4.8 MHz), whilst passing frequencies in the analogue signal that are between these threshold values.

The bandpass filtered analogue is preferably then converted by the analogue to digital converter 160 into a digital signal at a sample rate that is less than two times the bandwidth of the bandpass filtered analogue signal using a bandpass sampling technique. The microprocessor 150 then produces echo data representative of reflected ultrasound energy received by the ultrasound transducer 122 based on the digital signal.

The rotary encoder 170 may be an optical encoder, e.g. a low cost optical encoder with a 0.25° angular resolution. The rotary encoder 170 may produce a signal representative of an angle of rotation of the head 120 relative to the housing 130. The microprocessor 150 may be configured to produce position/orientation data representative of the position and orientation of the ultrasound transducer 122 on the first side 105a of the surface 105 during each collection cycle based on this signal.

On completion of a journey along the predetermined arc 124, the position/orientation data and echo data is preferably transmitted via the cable 122 to be acquired by the processing unit 180.

The processing unit 180 preferably then forms a B-mode (2D) ultrasound image of the target region 105c from the position/orientation data and the echo data acquired on completion of the predetermined arc 124. To coherently focus the echo data for a particular point in the target area, the processing unit may coherently sum the echo data corresponding to that point arising from each of the transducer positions along the predetermined arc which insonify that point. Therefore the processing unit preferably calculates which transducer positions are to be included in the summation, apply an appropriate time delay and/or phase shift to each of the included echo data and then sum each of the time delayed and/or phase shifted echo data. This process is preferably repeated for a plurality of points across the whole of the target area.

Traditionally, "synthetic array" techniques use signals acquired along a straight line trajectory, rather than an arc 124 (as in the proposed device). Therefore, some modification of standard "synthetic array" techniques is required in order to achieve focusing. A reason it is preferred for the ultrasound transducer 122 to be moved along a predetermined arc 124 is that this permits a wide field of view to be insonified with a relatively small amount of movement (albeit with a modest loss in image quality).

Preferably, as the ultrasound transducer 122 is repeatedly moved backwards and forwards along the predetermined arc 124, the proceeding unit 180 preferably produces a plurality of ultrasound images of the target region 105c, wherein each ultrasound image is produced from position/orientation data and echo data acquired from a respective journey of the ultrasound transducer 122 along the predetermined arc 124 and preferably regardless of the direction of movement of the ultrasound transducer 122 along the predetermined arc 124.

Thus, by manually moving the ultrasound transducer 122 backwards and forwards along the predetermined arc, several ultrasound images can be generated per second, meaning that near real-time observation of the structure in the target region is possible.

In general terms, the above discussion can be viewed as describing a preferred example of our proposals that that may provide a low cost ultrasound imaging apparatus including a manually scanned single ultrasound transducer head, with integral electronics, that may be connected to any standard windows PC, e.g. via a USB 2 interface or later. As the ultrasound transducer is manually swept over skin in a predetermined arc defined by a rotary mechanism (see e.g. FIG. 2), echo data from successive transmitted ultrasound pulses is preferably transmitted to a PC along with angle registration data for each position at which a pulse is transmitted. On completion of a full sweep, the PC application then treats this signal data as coming from a convex ultrasound array and coherently focuses the echo data from every point in a target area that has been insonified to produce an ultrasound image.

Figure 5:
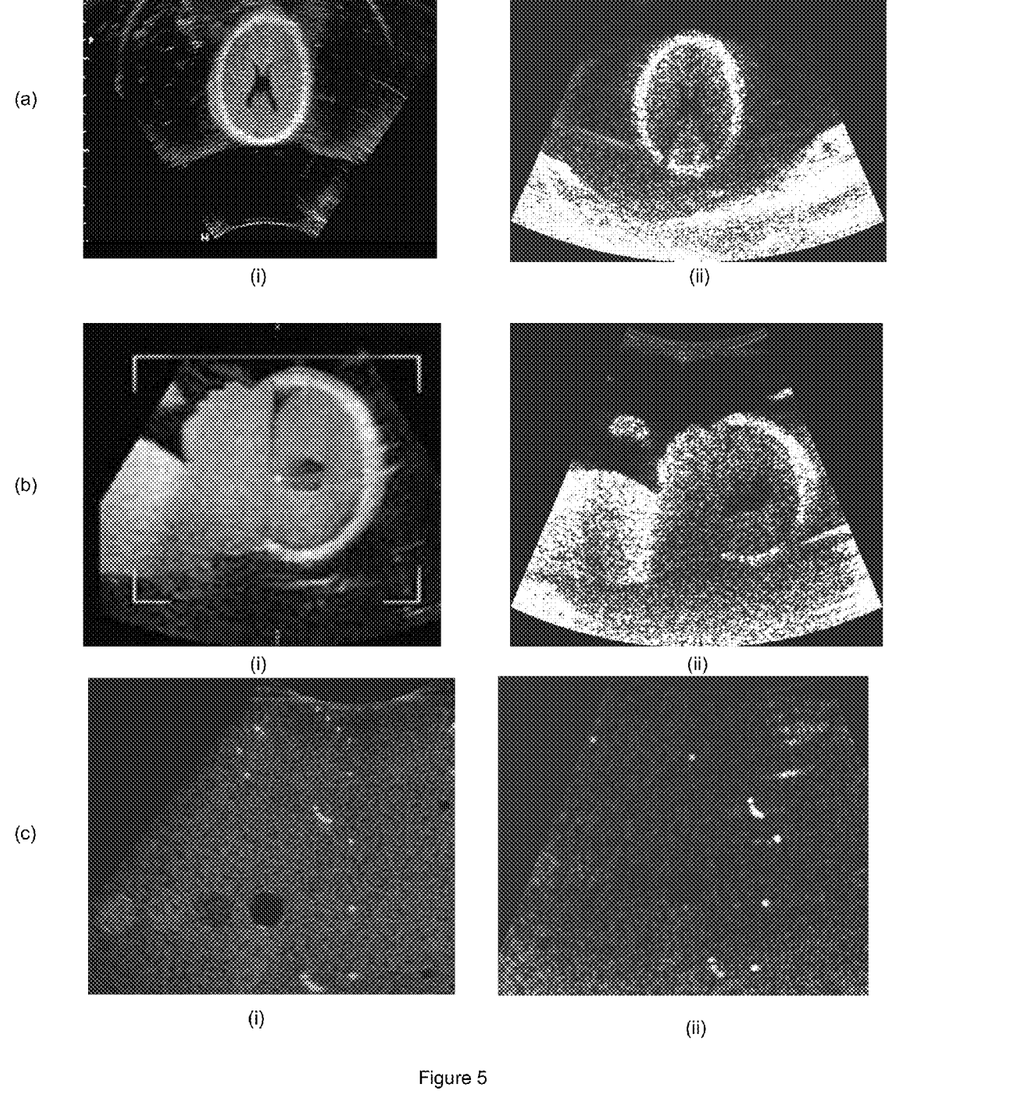
FIG. 5 is a collection of ultrasound images comparing ultrasound images produced by a commercially available ultrasound imaging apparatus with ultrasound images produced by the ultrasound imaging apparatus of FIG. 1.

FIG. 5 is a collection of ultrasound images comparing ultrasound images produced by a commercially available ultrasound imaging apparatus with ultrasound images produced by the ultrasound imaging apparatus of FIG. 1, applied to the same phantom target devices.

In FIG. 5, the ultrasound images labelled (i) were produced by the commercially available ultrasound imaging apparatuses being sold for £50,000-£100,000 (2012 prices), and the ultrasound images labelled (ii) were produced by the ultrasound imaging apparatus of FIG. 1. In more detail:

FIG. 5(a)(i),(ii) show the cross section of a head showing ventricles;

FIG. 5(b)(i),(ii) show the profile of a face and head;

FIG. 5(c)(i),(ii) show a resolution/contrast phantom (liver tissue).

The ultrasound images labelled (ii) in FIG. 5 show that the ultrasound imaging apparatus 100 built according to the principles described herein is capable of producing usable ultrasound images, despite using components which cost a small fraction of those contained in the commercially available ultrasound imaging apparatus.

When used in this specification and claims, the terms "comprises" and "comprising", "including" and variations thereof mean that the specified features, steps or integers are included. The terms are not to be interpreted to exclude the possibility of other features, steps or integers being present.

The features disclosed in the foregoing description, or in the following claims, or in the accompanying drawings, expressed in their specific produces or in terms of a means for performing the disclosed function, or a method or process for obtaining the disclosed results, as appropriate, may, separately, or in any combination of such features, be utilised for realising the invention in diverse produces thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the scope of the invention.

All references referred to above are hereby incorporated by reference.

The invention claimed is:

1. An ultrasound imaging apparatus including:
   a single ultrasound transducer that has a fixed focal length, the single ultrasound transducer being configured to perform, in each of a plurality of positions and/or orientations on a first side of a surface, a respective collection cycle in which the ultrasound transducer emits ultrasound energy into and receives reflected ultrasound energy from a target region on a second side of the surface that is opposite to the first side;
   a processing unit configured to acquire echo data representative of reflected ultrasound energy received by the single ultrasound transducer during each collection cycle and position/orientation data representative of the position and/or orientation of the ultrasound transducer on the first side of the surface during each collection cycle;
   wherein the processing unit is configured to produce an ultrasound image of the target region by applying the position/orientation data to the echo data so as to coherently focus the echo data at a plurality of points distributed within the target region, and
   wherein the processing unit coherently focuses the echo data at the plurality of points distributed within the target region by, for each respective point of the plurality of points distributed in the target region:
   (i) calculating which transducer positions/orientations to include in a summation corresponding to the respective point,
   (ii) applying a time delay and/or phase shift to echo data corresponding to each transducer position/orientation to be included in the summation, and
   (iii) summing the time delayed and/or phase shifted echo data.

2. An ultrasound imaging apparatus according to claim 1, wherein the ultrasound transducer is included in an ultrasound probe that is separate from the processing unit.

3. An ultrasound imaging apparatus according to claim 2, wherein the ultrasound probe includes:
   a head to which the ultrasound transducer is mounted; and
   a housing to which the head is moveably mounted so as to allow the ultrasound transducer to be moved relative to the housing along a predetermined path.

4. An ultrasound imaging apparatus according to claim 3, wherein the ultrasound probe is manually operable, with the head being movably mounted to the housing so as to allow the ultrasound transducer to be moved relative to the housing along a predetermined path by a hand of a user.

5. An ultrasound imaging apparatus according to claim 3, wherein the head and housing are sized so that the housing can be held in a first hand of a user while the head is moved relative to the housing by a second hand of the user.

6. An ultrasound imaging apparatus according to claim 3, wherein the head is rotatably mounted to the housing so as to allow the ultrasound transducer to be moved relative to the housing along a predetermined curved path.

7. An ultrasound imaging apparatus according to claim 6, wherein the curved predetermined path is convex in relation to the surface.

8. An ultrasound imaging apparatus according to claim 3, wherein:
   the plurality of positions and/or orientations in which collection cycles are performed by the ultrasound transducer correspond to a plurality of predetermined locations on the predetermined path; and
   the ultrasound transducer is configured to perform a collection cycle at each of the predetermined locations on the predetermined path based on a signal representative of a position and/or orientation of the head relative to the housing.

9. An ultrasound imaging apparatus according to claim 8, wherein the mean distance between the predetermined locations on the predetermined path is half the width or less than the width of an ultrasound-emitting face of the ultrasound transducer.

10. An ultrasound imaging apparatus according to claim 3, wherein echo data is acquired from multiple journeys of the ultrasound transducer along the predetermined path, wherein the processing unit is configured to produce a plurality of ultrasound images of the target region, wherein each ultrasound image is produced from position/orientation data and echo data acquired from each respective journey of the ultrasound transducer along the predetermined path.

11. An ultrasound imaging apparatus according to claim 10, wherein echo data is acquired from multiple journeys of the ultrasound transducer along the predetermined path, wherein the processing unit is configured to produce each ultrasound image from position/orientation data and echo data acquired from each respective journey of the ultrasound transducer along the predetermined path regardless of a direction of movement of the ultrasound transducer along the predetermined path.

12. An ultrasound imaging apparatus according to claim 1, wherein the ultrasound transducer has a focal length of 5 mm or less in a plane of the image generation.

13. An ultrasound imaging apparatus according to claim 1, wherein the ultrasound transducer is a single ultrasound transducer element having an ultrasound-emitting face which has a width of 3 mm or less, or less than 10 signal wavelengths, in the plane of the image generation.

14. An ultrasound imaging apparatus according to claim 1, wherein the ultrasound transducer is included in an ultrasound probe, the ultrasound probe including a position/orientation data unit configured to produce the position/orientation data representative of the position and/or orientation of the ultrasound transducer on the first side of the surface during each collection cycle.

15. An ultrasound imaging apparatus according to claim 14, wherein the position/orientation data unit includes:
- a position and/or orientation determining unit for producing a signal representative of a position and/or orientation of the head relative to the housing; and
- a processing means configured to produce the position/orientation data based on the signal representative of a position and/or orientation of the head relative to the housing.

16. An ultrasound imaging apparatus according to claim 1, wherein the ultrasound transducer is included in an ultrasound probe, the ultrasound probe including an echo data acquisition unit configured to produce the echo data representative of reflected ultrasound energy received by the ultrasound transducer during each collection cycle.

17. An ultrasound imaging apparatus according to claim 16, wherein the echo data acquisition unit includes:
- an analogue to digital converter configured to convert an analogue signal representative of reflected ultrasound energy received by the ultrasound transducer during each collection cycle into a digital signal representative of reflected ultrasound energy received by the ultrasound transducer during each collection cycle; and
- a bandpass filter for filtering the analogue signal before it reaches the analogue to digital converter;
- wherein the analogue to digital converter is configured to convert the bandpass filtered analogue signal into the digital signal at a sample rate that is less than two times the bandwidth of the bandpass filtered analogue signal using a bandpass sampling technique.

18. An ultrasound imaging apparatus according to claim 1, wherein the plurality of points are distributed at a plurality of depths within the target region.

19. An ultrasound imaging apparatus according to claim 1, wherein the ultrasound image is a 2D ultrasound image of the target region.

20. An ultrasound imaging apparatus according to claim 1, wherein the single ultrasound transducer is an unfocussed ultrasound transducer that does not include an acoustic lens.

21. A method of producing an ultrasound image, the method including:
- performing, in each of a plurality of positions and/or orientations on a first side of a surface, a respective collection cycle in which a single ultrasound transducer that has a fixed focal length emits ultrasound energy into and receives reflected ultrasound energy from a target region on a second side of the surface that is opposite to the first side;
- acquiring echo data representative of reflected ultrasound energy received by the single ultrasound transducer during each collection cycle and position/orientation data representative of the position and/or orientation of the ultrasound transducer on the first side of the surface during each collection cycle; and
- producing an ultrasound image of the target region by applying the position/orientation data to the echo data so as to coherently focus the echo data at a plurality of points distributed within the target region,
- wherein coherently focussing the echo data and the plurality of points distributed within the target region includes, for each respective point of the plurality of points distributed region: calculating which transducer positions/orientations to include in a summation corresponding to the respective point, applying a time delay and/or phase shift to echo data corresponding to each transducer position/orientation to be included in the summation, and summing the time delayed and/or phase shifted echo data.

* * * * *